United States Patent
Le Gallo-Bourdeau et al.

(10) Patent No.: US 10,424,370 B2
(45) Date of Patent: Sep. 24, 2019

(54) SENSOR DEVICE WITH RESISTIVE MEMORY FOR SIGNAL COMPRESSION AND RECONSTRUCTION

(71) Applicant: International Business Machines Corporation, Armonk, NY (US)

(72) Inventors: Manuel Le Gallo-Bourdeau, Zurich (CH); Abu Sebastian, Adliswil (CH); Giovanni Cherubini, Rueschlikon (CH)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/031,041

(22) Filed: Jul. 10, 2018

(65) Prior Publication Data
US 2019/0122727 A1   Apr. 25, 2019

Related U.S. Application Data

(60) Provisional application No. 62/576,084, filed on Oct. 24, 2017.

(51) Int. Cl.
| | |
|---|---|
| *G11C 13/00* | (2006.01) |
| *G06F 17/16* | (2006.01) |
| *H04N 5/378* | (2011.01) |
| *G06T 9/00* | (2006.01) |
| *G06K 9/40* | (2006.01) |
| *H03M 1/12* | (2006.01) |
| *A61B 5/00* | (2006.01) |

(52) U.S. Cl.
CPC .......... *G11C 13/0004* (2013.01); *G06F 17/16* (2013.01); *G11C 13/004* (2013.01); *G11C 13/0064* (2013.01); *G11C 13/0069* (2013.01); *H04N 5/378* (2013.01); *A61B 5/0033* (2013.01); *G06K 9/40* (2013.01); *G06T 9/00* (2013.01); *G11C 2213/79* (2013.01); *H03M 1/12* (2013.01)

(58) Field of Classification Search
CPC ... H03M 1/12; G06K 9/40; G06T 9/00; A61B 5/0033
USPC .......... 341/126, 155; 382/232, 275, 299, 131
See application file for complete search history.

(56) References Cited

U.S. PATENT DOCUMENTS

| | | |
|---|---|---|
| 8,749,422 B1 | 6/2014 | Moore |
| 8,982,260 B2 | 3/2015 | Eshraghian et al. |

(Continued)

OTHER PUBLICATIONS

Massoud, Y., et al., "A Memristor-Based Random Modulator for Compressive Sensing Systems", Conference Paper, May 2012, pp. 2245-2448.

(Continued)

*Primary Examiner* — Joseph J Lauture
(74) *Attorney, Agent, or Firm* — Scully, Scott, Murphy & Presser, P.C.; Daniel P. Morris, Esq.

(57) ABSTRACT

A sensor device comprising a computational memory and electronic circuitry. The sensor device is configured to receive an input signal, to compress the input signal into a compressed signal and to compute a reconstructed signal from the compressed signal. The electronic circuitry is configured to perform a reconstruction algorithm to compute the reconstructed signal. The computational memory is configured to compute the compressed signal and partial results of the reconstruction algorithm. A related method and a related design structure may be provided.

18 Claims, 5 Drawing Sheets

(56) References Cited

U.S. PATENT DOCUMENTS

| | | | |
|---|---|---|---|
| 2006/0029279 A1* | 2/2006 | Donoho | G06K 9/0057 382/232 |
| 2015/0372805 A1 | 12/2015 | Yoon | |
| 2018/0046598 A1 | 2/2018 | Le Gallo et al. | |
| 2018/0067720 A1 | 3/2018 | Bekas et al. | |

OTHER PUBLICATIONS

Shukai, D., et al., "Analog memristive memory with applications in audio signal processing", Science China Information Sciences, Research Paper, Received Jan. 14, 2013, Accepted Feb. 19, 2013, pp. 1-15.

Liu S. et al., "Ultra-Fast Robust Compressive Sensing Based on Memristor Crossbars", Draft, Sep. 19, 2016, pp. 1-10.

Oike, Y., et al., "CMOS Image Sensor With Per-Column ΣΔ ADC and Programmable Compressed Sensing", IEEE Journal of Solid-State Circuits, Jan. 2013, pp. 318-328, vol. 48, No. 1.

Maechler, P., et al., "VLSI Design of Approximate Message Passing for Signal Restoration and Compressive Sensing", IEEE Journal on Emerging and Selected Topics in Circuits and Systems, Oct. 2012, 11 pages, vol. 2, No. 3.

Borghetti, J., et al., "Memristive' switches enable 'stateful' logic operations via material implication", Nature, Apr. 8, 2010, pp. 873-976, vol. 464.

Ievlev, A.V., et al., "Intermittency, quasiperiodicity and chaos in probe-induced ferroelectric domain switching", Nature Physics, Published online Nov. 17, 2013, Jan. 2014, pp. 59-66, vol. 10.

Di Ventra, M., et al., "The parallel approach", Nature Physics, Apr. 2013, pp. 200-202, vol. 9.

Hosseini, C., et al., "An optoelectronic framework enabled by low-dimensional phase-change films", Nature, Jul. 10, 2014, pp. 206-211, vol. 511.

Burr, G.W., et al., "Experimental demonstration and tolerancing of a large-scale neural network (165,000 synapses), using phase-change memory as the synaptic weight element", Proc. IEDM, Dec. 17, 2014, pp. 29.5.4-29.5-4.

Prezioso, M., et al., "Training and operation of an integrated neuromorphic network based on metal-oxide memristors", Nature, May 7, 2015, pp. 61-64, vol. 521.

Gupta, S., et al., "Deep Learning with Limited Numerical Precision", arXiv, Feb. 9, 2015, pp. 1-10.

Donoho, D., et al., "Message-passing algorithms for compressed sensing", PNAS, Sent for review Jul. 21, 2009, Nov. 10, 2009, pp. 18914-18919, vol. 106, No. 45.

Bayati, M., et al., "The Dynamics of Message Passing on Dense Graphs, with Applications to Compressed Sensing", IEEE Transactions on Information Theory, Feb. 2011, pp. 764-785, vol. 57, No. 2.

* cited by examiner

SENSOR DEVICE WITH RESISTIVE MEMORY FOR SIGNAL COMPRESSION AND RECONSTRUCTION

BACKGROUND

The basic idea of compressed sensing is to reconstruct a high-dimensional signal from a small number of measurements. The compressive measurements can be thought of as a linear mapping of a signal $x_0$ of length N to a measurement vector y of length M<N. This process can be modeled by a M×N measurement matrix A.

The compressed sensing reconstruction problem is to determine the signal $x_0$ from the measurements y when sampled as $$y = Ax_0 + w;$$

wherein w represents the measurement noise.

Compressed sensing asserts that signals can be recovered from fewer samples than dictated by the Shannon-Nyquist theorem if they are sparse, that is, it allows to reconstruct a signal by finding a solution to an underdetermined linear system if the signal is sparse in some transform domain. If the signal $x_0$ is sparse in some transform domain, i.e. $x_0 = \Psi \xi$ where $\xi$ is sparse, it can be shown that if $\Psi$ is incoherent with A, then $\xi$ can be recovered when M<N. $\Psi$ represents the inverse transform matrix, for example an inverse Wavelet transform.

Compressed sensing can be used in various applications such as MRI, facial recognition, holography, audio restoration or in mobile phone camera sensors. In a camera sensor, the approach allows e.g. to significantly reduce the acquisition energy per image (or equivalently increase the image frame rate) by capturing only few measurements (e.g. 10%) instead of the whole image. However, this comes at the cost of complex reconstruction algorithms.

SUMMARY

According to a first aspect, the invention is embodied as a sensor device comprising a computational memory and electronic circuitry. The sensor device is configured to receive an input signal, to compress the input signal into a compressed signal and to compute a reconstructed signal from the compressed signal. The electronic circuitry is configured to perform a reconstruction algorithm to compute the reconstructed signal. The computational memory is configured to compute the compressed signal and partial results of the reconstruction algorithm.

According to an embodiment of another aspect of the invention, a method for signal compression and reconstruction is provided. The method is performed by a sensor device which comprises a computational memory and electronic circuitry. The method comprises steps of receiving, by the sensor device, an input signal and computing, by the computational memory, a compressed signal from the input signal. The method comprises a further step of performing, by the electronic circuitry, a reconstruction algorithm to compute a reconstructed signal from the compressed signal. Further steps include computing, by the computational memory, partial results of the reconstruction algorithm and providing, by the computational memory, the partial results to the electronic circuitry for a further processing of the reconstruction algorithm.

According to another aspect a design structure is provided. The design structure is tangibly embodied in a machine readable medium for designing, manufacturing, or testing an integrated circuit. The design structure comprises a sensor device comprising a computational memory and electronic circuitry. The sensor device is configured to receive an input signal, to compress the input signal into a compressed signal and to compute a reconstructed signal from the compressed signal. The electronic circuitry is configured to perform a reconstruction algorithm to compute the reconstructed signal. The computational memory is configured to compute the compressed signal and partial results of the reconstruction algorithm.

Embodiments of the invention will be described in more detail below, by way of illustrative and non-limiting examples, with reference to the accompanying drawings.

DETAILED DESCRIPTION

In reference to FIGS. 1-8, some general aspects and terms of embodiments of the invention are described.

According to embodiments of the invention, a resistive memory element may be defined as a memory element whose electrical resistance can be changed by applying an electrical programming signal to the resistive memory element. The electrical programming signal may be e.g. a current flowing through the resistive memory element, or an electrical voltage applied to the resistive memory element. The current and/or voltage may be e.g. applied to the resistive memory element in the form of pulses. As a result, the electrical resistance of a resistive memory element depends on the history of current that had previously flown through the memory element and/or the history of the electric signal that had been applied to the resistive memory element.

Resistive memory elements are based on a physical phenomenon occurring in a material that changes its resistance under action of a current or electric field. The change is usually non-volatile and reversible. Several classes of resistive memory elements are known, ranging from metal oxides to chalcogenides. Typical resistive memory elements are metal/insulator/metal structures where the metallic components serve as the electrodes and the insulator is a resistive switching material, e.g. a chalcogenide. These resistive memory elements exhibit good performance in terms of power consumption, integration density potential, retention, and endurance.

Memcomputing is a non-Von Neumann approach being researched. An element in this computing paradigm is a computational memory. The computational memory may comprise high-density, low-power, variable state, programmable and non-volatile memory devices.

A computational primitive is a matrix-vector multiplication. This primitive is of particular interest as it forms the basis of several linear algebraic operations and it is one of the most commonly used mathematical operations in science and engineering. A matrix is usually represented by a two-dimensional array of matrix elements and a vector by a one-dimensional array of vector elements. A matrix may be considered as array of vectors. Hence a matrix-vector multiplication can be generalized to a matrix-matrix multiplication and to a vector-vector multiplication.

According to embodiments of the invention a computational memory may be used to perform certain low-level computational tasks of sensor devices, in particular matrix vector multiplications for signal compression and reconstruction.

Such computational memory may, for example, be implemented as an interconnected array of nanoscale resistive memory devices, or memristor arrays. These arrays may be made compact due to the density of the memristors within the array, and the overall energy efficiency of the devices may be better than that achieved by systems using von Neumann architectures to perform similar computations.

Figure 1:
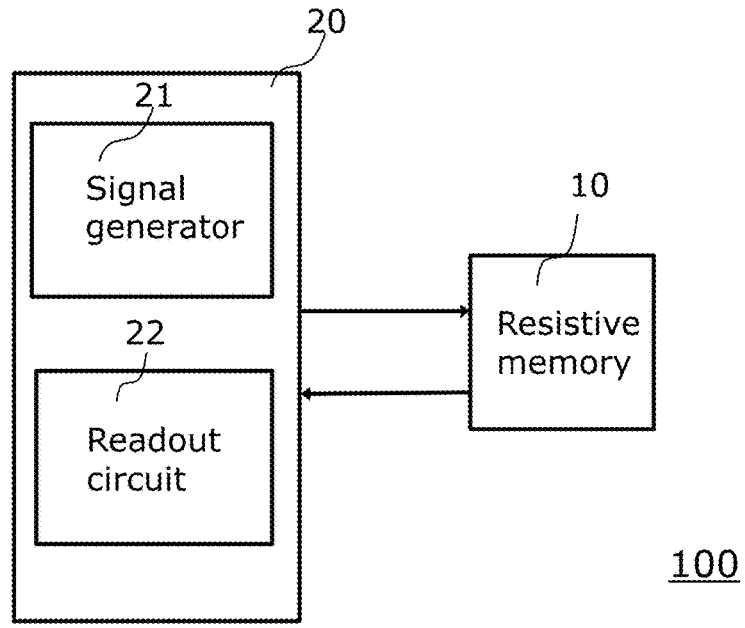
FIG. 1 is a simplified schematic block diagram of a sensor device according to embodiments of the invention.

FIG. 1 is a simplified schematic block diagram of a sensor device 100 according to embodiments of the invention. The sensor device 100 comprises electronic circuitry 20 and a resistive memory 10 having a plurality of resistive memory elements. The resistive memory 10 serves as computational memory and may accordingly also be denoted as computational memory 10. The electronic circuitry 20 encompasses a signal generator 21 and a readout circuit 22. The signal generator 21 is configured to apply electrical programming signals to the resistive memory elements of the resistive memory 10. The signal generator 21 comprises circuitry for programming the resistive memory cells during data write or programming operations such that a multiplication of a matrix with a vector can be performed. During these write operations, the signal generator 21 can address individual memory cells by applying appropriate control signals to an array of row lines and column lines in the resistive memory 10. The row lines and column lines may also be denoted as word and bit lines.

The signal generator 21 may be configured to receive a matrix A, in particular a measurement matrix, as input and to apply programming signals to the memory elements to program conductance values of the resistive memory elements as a measurement matrix for subsequent matrix-vector multiplications. The conductance values represent measurement matrix values of the measurement matrix that shall be multiplied with the respective vectors.

In addition, the device 100 comprises a readout circuit 22 configured to read out resistance values of the resistive memory elements during data read operations. More particularly, the sensor device 100 is configured to apply read out voltages to the rows and/or columns of memristive arrays of the resistive memory 10. The read out voltages represent vector elements of the vector that shall be multiplied with the matrix. The device is further configured to read out current values of columns and/or rows of the memristive array. The current values represent result values of vector elements of a result vector of the respective matrix-vector multiplication.

The resistive memory 10 may be generally any kind of resistive memory as described above. In particular it may be a phase change memory (PCM) or a resistive random access memory (RRAM). In the following it assumed that the resistive memory 10 is embodied as PCM. Accordingly the resistive memory 10 may comprise a plurality of PCM cells as resistive memory elements. The PCM cells of memory 10 may comprise s=2 or s>2 programmable resistance states, the latter providing multilevel operation. The s programmable resistance-states correspond to different relative proportions of the amorphous and crystalline phases within the PCM material of the cell. These states may include a high-resistance, fully-amorphous RESET state, a low-resistance, fully-crystalline SET state, and a number of intermediate states corresponding to increasing size of the crystalline phase within the otherwise amorphous PCM material. The s programmable cell-states are typically defined in terms of predetermined reference values, or ranges of values, of the resistance metric used for read detection by the readout circuit 22.

To perform a matrix-vector multiplication, the PCM cells are programmed according to embodiments in a kind of write operation. More particularly, the signal generator 21 applies a voltage to the cell via the column lines and row lines such that the resulting programming signal sets the cell to a state (conductance value) that represents a matrix element of the measurement matrix that shall be multiplied with the respective vector in subsequent operations. In a read operation, (lower) read voltages are applied to the row and/or column lines. Then the resulting column current values row and/or row current values are read/measured to obtain the result vector.

Figure 2:
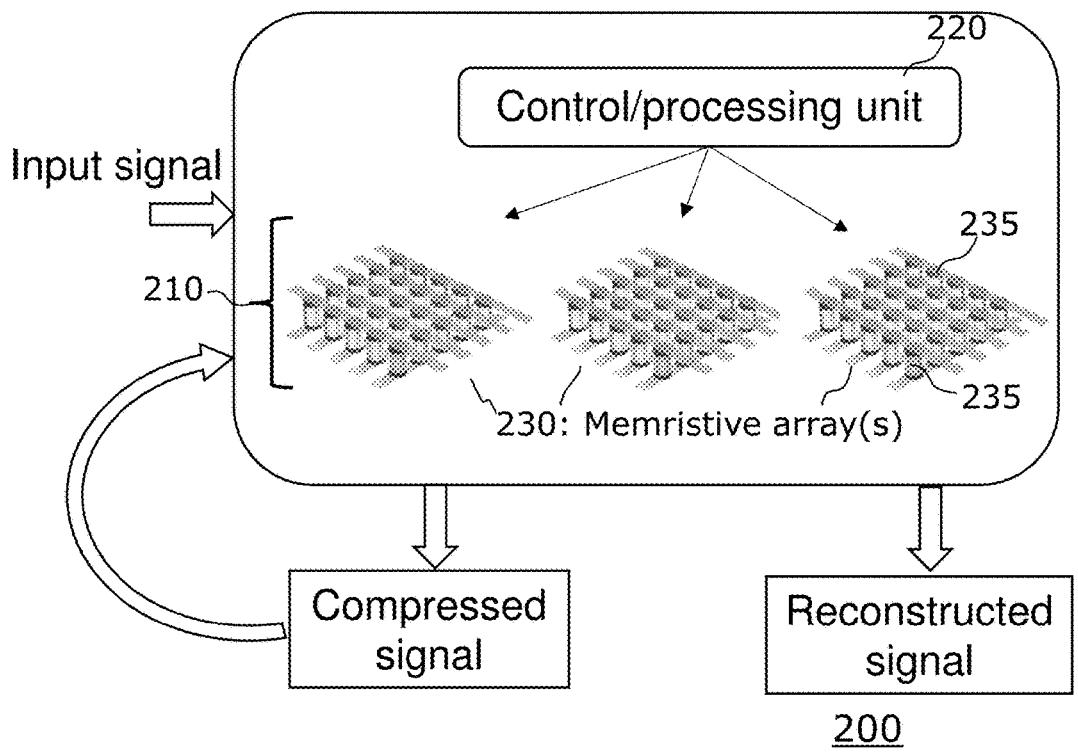
FIG. 2 illustrates schematically the operation of a sensor device according to an embodiment of the invention.

FIG. 2 illustrates schematically the operation of a sensor device 200 according to an embodiment of the invention. The sensor device 200 comprises a control/processing unit 220 which includes electronic circuitry and a computational memory 210 embodied as resistive memory 210. The resistive memory 210 comprises a plurality of memristive arrays 230 comprising a plurality of resistive memory elements 235. The resistive memory elements 235 are arranged in a crossbar topology.

In operation the sensor device 200 receives an input signal, in particular a measurement signal from a sensor measurement, and compresses the input signal into a compressed signal. The compression is performed by means of the computational memory 210. More particularly, the computational memory 210 compresses the input signal by performing a matrix-vector multiplication of the input signal with a measurement matrix that has been programmed to one of the memristive arrays 230.

Furthermore, the sensor device 200 computes a reconstructed signal from the compressed signal. More particularly, the electronic circuitry of the control/processing unit 220 performs a reconstruction algorithm, in particular an approximate message passing algorithm. During the execution of the reconstruction algorithm, the computational memory 210 computes partial results of the reconstruction algorithm and provides these partial results back to the control/processing unit 220. More particularly, the computational memory 210 computes the partial results of the reconstruction algorithm by performing matrix-vector multiplications with the measurement matrix. The partial results may establish intermediate state variables of the reconstruction algorithm. The control/processing unit 220 uses then these partial results for the further processing of the reconstruction algorithm. After a sufficient number of T iterations of the reconstruction algorithm, the control/processing unit 220 may output the final reconstructed signal.

Hence such an embodied sensor provides the advantage that the compression as well as the reconstruction is performed on the sensor device itself. This is in contrast to conventional sensor devices that often require an off-device implementation of the reconstruction algorithm.

This is in particular useful for Internet of Things (IoT systems). The processing of the compressed signal and the partial results of the reconstruction algorithm may be performed by the computational memory with very low power. This allows energy-efficient signal acquisition while at the same time avoiding to send the compressed signal e.g. to the cloud for reconstruction.

Accordingly, compared with compression and reconstruction techniques based on the conventional Von-Neumann approach, sensor devices according to embodiments of the invention may bring significant power and/or speed advantages.

Figure 3:
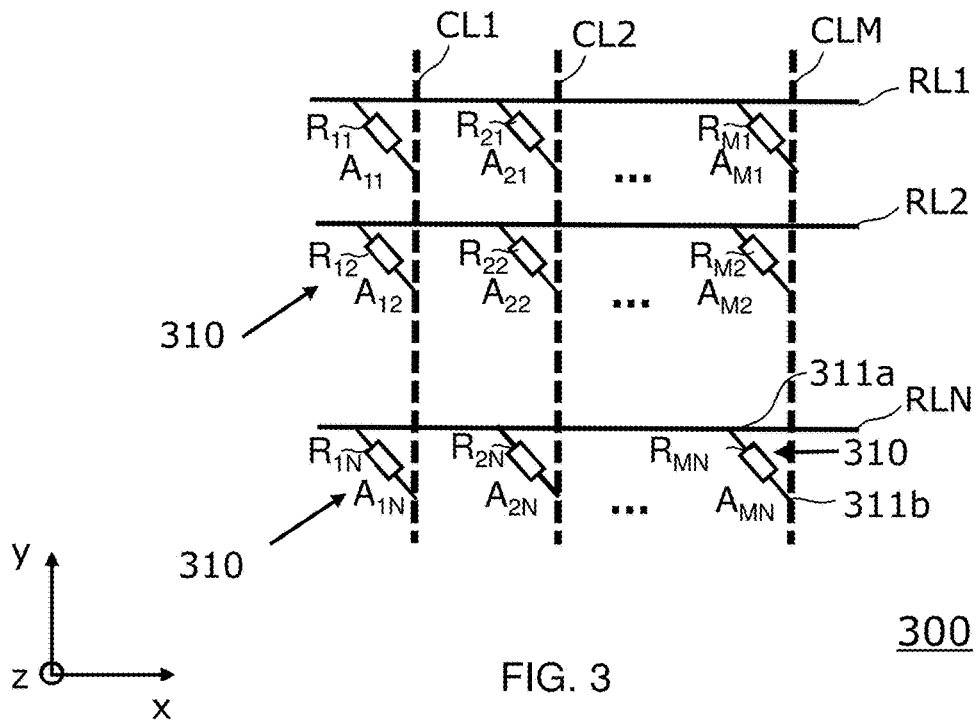
FIG. 3 illustrates schematically a memristive array of a computational memory according to an embodiment of the invention that has been programmed as a measurement matrix M×N.

FIG. 3 illustrates schematically a memristive array 300 of a computational memory according to an embodiment of the invention that has been programmed as a measurement matrix M×N.

The memristive array 300 comprises a plurality of row lines RL1, RL2, . . . , RLN and a plurality of column lines CL1, CL2, . . . , CLM. The row lines are arranged above the column lines which are indicated by dotted lines. More particularly, the row lines extend in a first x-y-plane and the column lines extend in a second x-y plane, wherein the first x-y plane is arranged in the vertical z-direction above the second x-y-plane.

The row lines and the column lines are connected to each other via vertical junctions 310. The junctions 310 extend in the vertical z-direction between upper cross points 311a of the row lines and lower cross points 311b of the column lines.

Each junction 310 comprises a serial arrangement of a resistive memory element $R_{mn}$ and a transistor. For ease of illustration, the transistors are not shown in FIG. 3.

In order to program the measurement matrix A, the signal generator 21 (see FIG. 1) applies programming signals, in particular current pulses, to the resistive memory elements $R_{mn}$ and thereby programs the conductance values for subsequent matrix-vector multiplications with the measurement matrix A. More particularly, the conductance values of the resistive memory elements $R_{mn}$ represent matrix values $A_{mn}$ of the measurement matrix A. As an example, the conductance of the resistive memory element $R_{11}$ is programmed to the matrix value $A_{11}$, the conductance of the resistive memory element $R_{12}$ is programmed to the matrix value $A_{12}$, or more generally the conductance of the resistive memory $R_{mn}$ is programmed to a corresponding matrix value $A_{mn}$.

According to embodiments, the M×N measurement matrix A may be programmed as device conductance values in one or multiple memristive arrays. In particular, according to embodiments the transpose A* of the measurement matrix A can be programmed in a separate memristive array.

One possible method to program the conductance values is using an iterative program-and-verify procedure. According to embodiments, the elements $A_{mn}$ of the measurement matrix A can be programmed on multiple devices/arrays, and the average conductance of the multiple devices/arrays may be used to represent one element of the measurement matrix A.

According to embodiments, A may contain negative elements and those negative elements may be coded separately from the positive ones together with a subtraction circuit.

Figure 4:
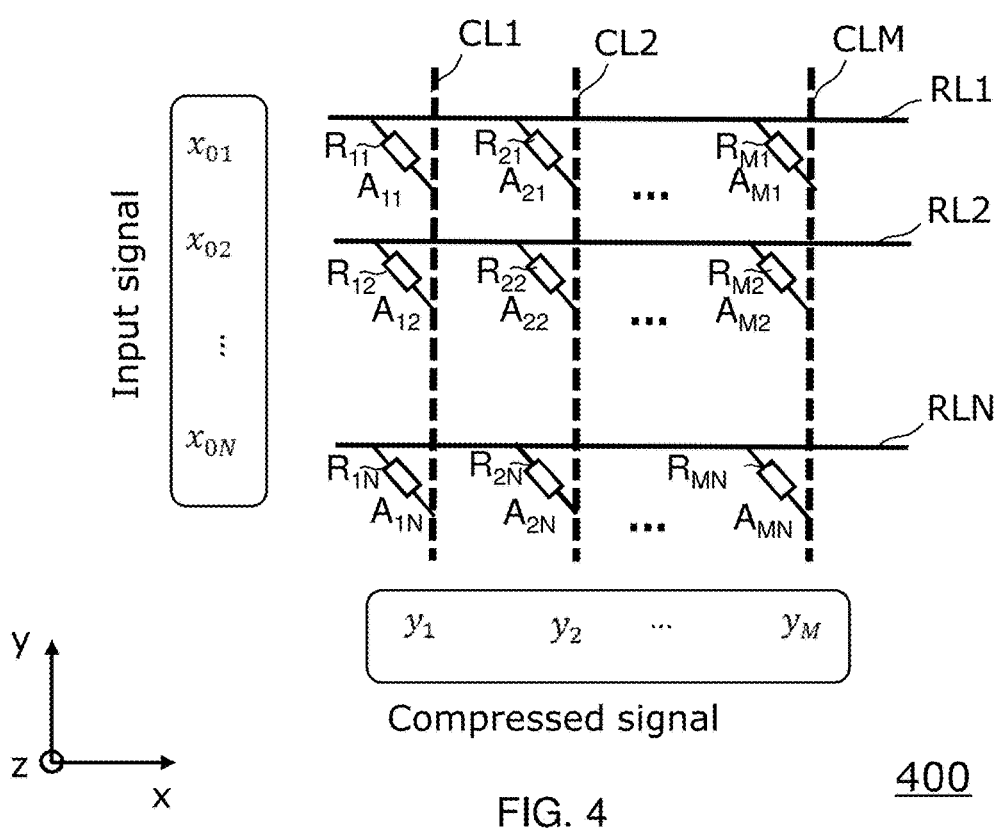
FIG. 4 illustrates the computation of a compressed signal from an input signal with a memristive array according to an embodiment of the invention.

FIG. 4 illustrates a compression of an input signal $x_0$ according to an embodiment of the invention. The compression is performed by means of a matrix-vector multiplication with the measurement matrix A.

The matrix-vector multiplication uses Ohm's law and Kirchhoff's law in a memristive array 400 which corresponds to the memristive array 300 as described with reference to FIG. 3.

The input signal $x_0$ comprises as vector elements the elements $x_{01}, x_{02}, \ldots, x_{0N}$. The readout circuit 22 (see FIG. 1) applies read voltages to the row lines. More particularly, the readout circuit 22 applies a read voltage $x_{01}$ to the row line RL1, a read voltage $x_{02}$ to the row line RL2 or generally a read voltage $x_{0n}$ to the row line RLn. Hence the read voltages represent vector values of the vector of the matrix-vector multiplication.

Furthermore, the readout circuit 22 reads out current values of the column lines CLm. As an example, the readout circuit 22 reads out a current value $y_1$ from the column line CL1 which is the sum of N multiplications, namely $$y_1 = A_{11}x_{01} + A_{12}x_{02} + \ldots + A_{1N}x_{0N}.$$

Accordingly, the readout circuit 22 reads out a current value $y_2$ from the column line CL2 and generally a current value $y_m$ from the column line CLm. The current values represent the result values of the vector elements of the product vector y. The product vector y forms the compressed signal of the input signal $x_0$.

Hence the input signal $x_0$ is compressed by applying it as voltage values at the input of the corresponding memristive array(s). The compressed signal y is obtained as the current signal at the output of the corresponding memristive array (s). The memristive crossbar array(s) essentially perform the operation $$y = Ax_0.$$

Figure 5:
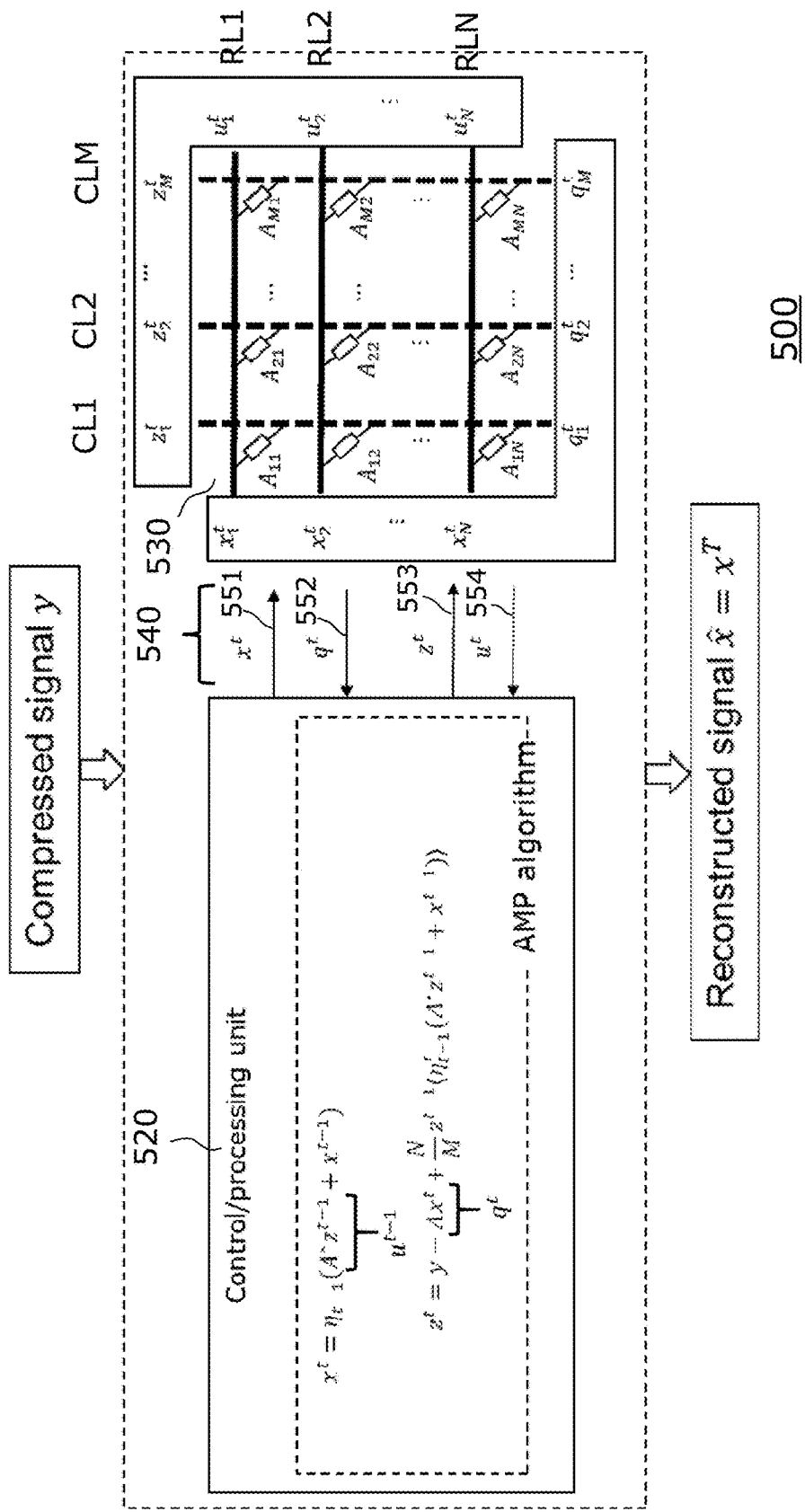
FIG. 5 illustrates an example embodiment of a computation of a reconstructed signal from the compressed signal by means of the sensor device.

FIG. 5 illustrates an example embodiment of the computation of a reconstructed signal $\hat{x} = x^T$ from the compressed signal y by means of a sensor device 500. The compressed signal y may be computed e.g. as illustrated with reference to FIG. 4. The computation of the reconstructed signal $\hat{x} = x^T$ is performed by executing a reconstruction algorithm. According to the example embodiment of FIG. 5, the reconstruction algorithm is an approximate message passing algorithm.

In general, an approximate message passing (AMP) algorithm solves the problem of reconstructing a vector $x_0 \in \mathbb{R}^N$ from a vector of linear observations $y \in \mathbb{R}^M$.

For example, a vector $x_0 \in \mathbb{R}^N$ may be reconstructed from a vector of linear observations $y \in \mathbb{R}^M$, such that $y = Ax_0 + w$. $A \in \mathbb{R}^{M \times N}$ is the known measurement matrix and $w \in \mathbb{R}^M$ is a noise vector $w \sim N(0, \sigma^2)$. The approximate message passing algorithm is an approximation to the following sum-product message passing algorithm. For all $n, n' \in [N] = \{1, 2, \ldots, N\}$ and $m, m' \in [M] = \{1, 2, \ldots, M\}$ start at time $t=0$ with messages $x_{n \to m}^0 = 0$ and proceed by $$z_{m \to n}^t = y_m - \sum_{n' \neq n} A_{mn'} x_{n' \to m}^t, \text{ and}$$

$$x_{n\to m}^{t+1} = \eta_t\left(\sum_{m'\neq m} A_{m'n} z_{m'\to n}^t\right),$$

where $z_{m\to n}^t$ represents the message passed from a function node $g_m$ to a variable node $x_{0n}$, $x_{n\to m}^t$ represents the message passed from a variable node to a function node and $\eta_t(\cdot)$ is a function.

An approximate message passing algorithm/technique may approximate a sum-product message passing technique in the large system limit, allowing updates of only $O(N)$ variables instead of $O(MN)$.

For example, a first order approximate message passing technique for reconstructing $x_0$ given A and y (Donoho et al., PNAS, 2009) may be represented as $$z^t = y - Ax^t + \frac{N}{M} z^{t-1} \langle \eta_{t-1}'(A*z^{t-1} + x^{t-1})\rangle;$$
$$x^{t+1} = \eta_t(A*z^t + x^t);$$

wherein $A*$ is the transpose of A, $\eta_t(\cdot)$ is a function, $\eta_t'(\cdot)$ its derivative, $\langle \cdot \rangle$ denotes the mean and $x^0=0$. The final value of $x^t$ may provide the estimate of $x_0$.

The AMP algorithm/technique may be equivalently formulated as an iterative thresholding process, which may provide the reconstruction power of other approaches, when sparsity of the solution may be assumed, at a much lower complexity. The AMP algorithm has a relatively simple formulation and requires only multiplications and additions.

For example, the AMP technique may be used to reconstruct a random vector $x_0 \in \mathbb{R}^N$, $x_{0n} \sim N(0, \rho^2)$, $\forall n$, from a vector of linear observations $y \in \mathbb{R}^M$, where $y = Ax_0 + w$, and $A \in \mathbb{R}^{M\times N}$ is a known measurement matrix. If a linear function $\eta_t(\cdot) = \lambda_t \times (\cdot)$ is chosen, the AMP technique/algorithm may be represented as $$x^{t+1} = \lambda_t(A*z^t + x^t);$$
$$z^t = y - Ax^t + \frac{N}{M} z^{t-1} \lambda_{t-1};$$

wherein $A*$ is the transpose of A, $x^0=0$ and $$\lambda_t = \frac{1}{1+\tau_t^2};$$
$$\tau_{t+1}^2 = \sigma^2 + \frac{N}{M}\frac{\tau_t^2}{\tau_t^2+1};$$

with $$\tau_0^2 = \sigma^2 + \frac{N}{M}\rho^2.$$

Here, $z^t$ and $x^t$ are the outgoing means of the random variables associated with the g and $x_0$ nodes, respectively, and $\lambda_t$ is a state variable. If $$A_{mn} \sim N\left(0, \frac{1}{M}\right)$$

(iid normalized Gaussian matrix), the convergence behavior of this algorithm may be given by $$\lim_{N\to\infty} \frac{1}{N}\|x^t - x_0\|^2 = (\tau_t^2 - \sigma^2)\frac{M}{N}.$$

The sensor device 500 comprises a control/processing unit 520 and a memristive array 530. The control/processing unit 520 and the memristive array 530 are coupled via a communication link 540 and may exchange data, in particular state variables and partial results of the reconstruction algorithm, via the communication link 540.

The control/processing unit 520 may control the operation and processing performed by the sensor device 500 and may typically be implemented by electronic circuitry including digital combinational logic. Memristive array 530 performs a portion of the computations that implement the AMP technique/algorithm, and may communicate with control/processing unit 520 using communication link 540, in particular to provide partial results of the reconstruction algorithm to the control/processing unit 520.

To reconstruct the compressed signal y, the AMP algorithm is run in the control/processing unit 520 for T iterations. The control/processing unit 520 provides $x^t$ at a step 551 to the memristive array 530. $x^t$ may be considered as a state variable of the AMP algorithm. More particularly, it provides $x^t$ to the row lines RL1, RL2, . . . , RLN of the memristive array 530. Then the memristive array 530 performs at a step 552 a matrix-vector multiplication of the measurement matrix A and $x^t$ and provides as partial result $$q^t = Ax^t$$

to the control/processing unit 520. More particularly, the memristive array 530 provides $q^t = Ax^t$ at the column lines CL1, CL2, . . . , CLM of the memristive array 530.

At a step 553, the control/processing unit 520 computes $$z^t = y - q^t + \frac{N}{M} z^{t-1} \langle \eta_{t-1}'(A*z^{t-1} + x^{t-1})\rangle$$

by utilizing the partial result $$q^t = Ax^t$$

and provides $z^t$ to the memristive array 510. More particularly, it provides $z^t$ as input to the column lines CL1, CL2, . . . , CLM of the memristive array 530.

At a step 554, the memristive array 530 performs a matrix-vector multiplication of the transpose $A*$ of the measurement matrix and $z^t$ and provides as partial result $$u^t = A*z^t$$

to the control/processing unit 520. More particularly, the memristive array 510 provides $u^t = A*z^t$ at the row lines RL1, RL2, . . . , RLN.

Finally, the control/processing unit 520 computes $$x^{t+1} = \eta_t(u^t + x^t)$$

by utilizing the partial result $$u^t = A*z^t$$

and provides $x^{t+1}$ to the memristive array 510 for the next AMP iteration.

Hence the computation of $q^t$ and $u^t$ is done using the one single memristive array 530, assuming appropriate read/write circuitry to apply voltages $x^t$ and $z^t$, and measure currents $q^t$ and $u^t$.

According to other embodiments, two separate memristive arrays may be provided, one for the computation of $q^t$ and one for the computation of $u^t$.

After T iterations, the reconstructed signal $\hat{x}=x^T$ is obtained.

According to embodiments, the reconstruction algorithm may comprise an integrated de-noising functionality. A general methodology for compressive imaging with AMP is introduced in [Metzler et al., From Denoising to Compressed Sensing, arXiv, 2014]. The algorithm may be written as $$z^t = y - Ax^t + z^{t-1} divD_{v^{t-1}}(A * z^{t-1})$$

$$x^{t+1} = D_{v^t}(A * z^t)$$

$$v_t^2$$

$$divD(x) = \sum_{i=1}^{N} \frac{\partial D(x)_i}{\partial x_i}$$

In this representation of the reconstruction algorithm D(x) denotes the denoiser and $v_t^2$ is an estimate of the variance of the noisy signal which is input to the denoiser.

Using a denoiser within AMP improves the signal reconstruction quality in the presence of measurement noise and also in the presence of the computational errors from the memristive array. According to embodiments, a denoiser may be designed which is specifically aimed at removing the errors due to computation in the memristive array in the reconstructed signal. Examples of denoisers are BM3D and wavelet denoisers with soft-thresholding. A wavelet denoiser transforms the signal into a wavelet basis, thresholds the coefficients, and then inverts the transform. An example is a Haar Wavelet transform and a soft-threshold function, defined as $D_{v^t}(x) = W^{-1} \eta_t(Wx)$, where:

$$\eta_t(x) = \begin{cases} x - \lambda v_t, & x \geq \lambda v_t \\ x + \lambda v_t, & x \leq -\lambda v_t \\ 0, & \text{otherwise} \end{cases}$$

The term $divD_{v^{t-1}}(A*z^{t-1}+x^{t-1})$ can be calculated explicitly and given by $\|\eta_{t-1}(W(A*z^{t-1}+x^{t-1}))\lambda_0$ (number of non-zero elements of thresholded sparsified estimate) where W denotes the wavelet transform.

According to another embodiment, a BM3D denoiser may be used. Block matching 3D collaborative filtering can be considered as a combination of non-local means (averaging neighboring weighted pixels) and wavelet thresholding. The term $divD_{v^{t-1}}(A*z^{t-1}+x^{t-1})$ cannot be calculated explicitly and may be estimated using a Monte-Carlo procedure as described e.g. in [Metzler et al., From Denoising to Compressed Sensing, arXiv, 2014]). BM3D may perform better on images than Wavelet thresholding because images are not exactly sparse in the Wavelet domain.

According to another embodiment, the sensor device is configured to perform a block-based compression and reconstruction. To compress and reconstruct e.g. a 128×128 image, the size of the vector $x_0$ (pixel intensities of the image) is N=16384. For such a large value of N it may require a very large number of devices (at least 10M) to code a Gaussian M×N matrix in the memristive array. According to one embodiment, a $M_S \times N_S$. Gaussian measurement matrix H may be used, in particular a much smaller measurement matrix, and consecutive measurements on pixel blocks may be performed using the same measurement matrix H. According to an embodiment, for example 16×16 pixels blocks may be used, and thus $N_S$=256. To ensure convergence of the AMP algorithm, a strategy according to an embodiment is to do a (fixed) random permutation P of the pixel intensities before doing the measurements. According to such an embodiment, each iteration of the AMP algorithm will require one permutation and one inverse permutation. More particularly, the matrix A may be given by $$A$$

$$A^*$$

wherein $$\text{Blockdiag}(H) = \begin{bmatrix} H & \cdots & 0 \\ \vdots & \ddots & \vdots \end{bmatrix}$$

Figure 6:
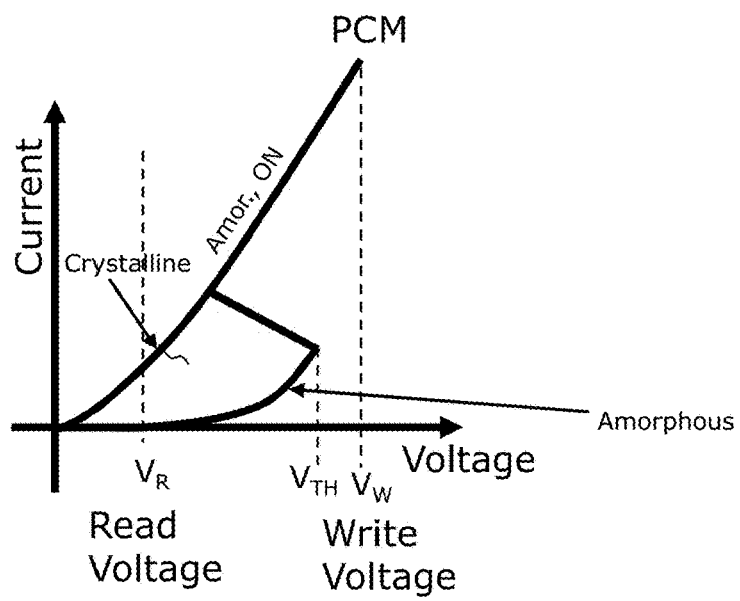
FIG. 6 is a schematic illustration of the current/voltage characteristics of the material components of a phase change memory cell.

FIG. 6 is a schematic illustration of the current/voltage (and hence resistance) characteristics of the material components of a PCM cell. The solid lines indicate variation of current with voltage for the PCM material, starting from the fully-crystalline SET state (upper curve) and also the fully-amorphous RESET state (lower curve). These two curves reflect the large (typically 3 orders of magnitude) variation in resistivity between the crystalline and amorphous phases. The amorphous phase exhibits a non-linear characteristic with a threshold switching phenomenon that is field induced. At a certain threshold voltage VTH, this phase switches to a very low "ON-state" resistance corresponding to that of the crystalline PCM material. The cell programming (write) voltage is selected to be above this threshold voltage as indicated.

Figure 7:
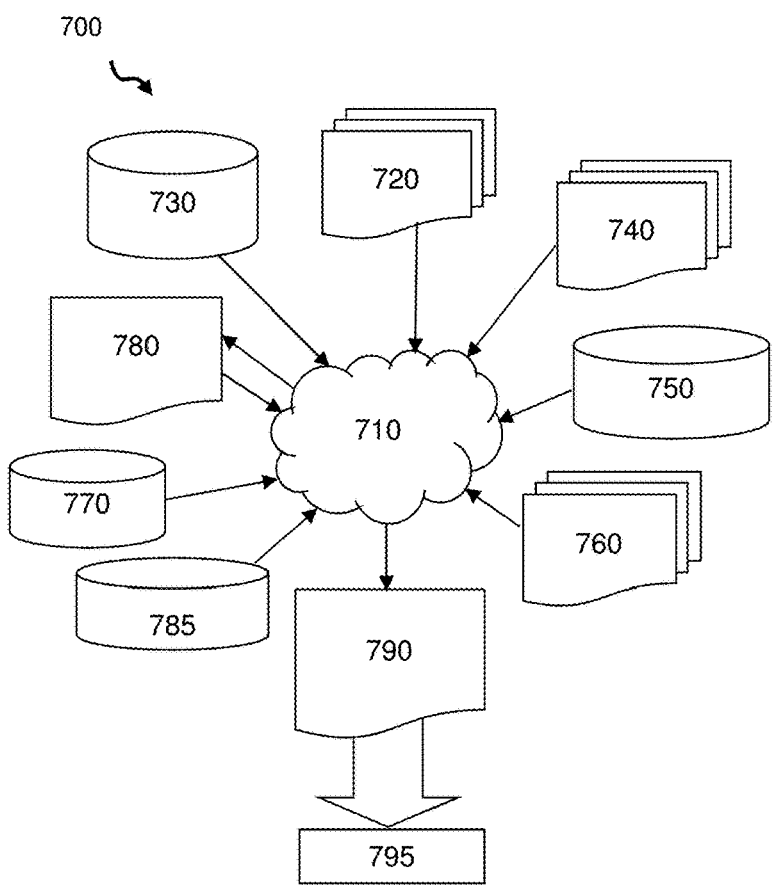
FIG. 7 shows a block diagram of an example design flow.

FIG. 7 shows a block diagram of an example design flow 700 used for example, in semiconductor IC logic design, simulation, test, layout, and manufacture. Design flow 700 includes processes, machines and/or mechanisms for processing design structures or devices to generate logically or otherwise functionally equivalent representations of the design structures and/or devices described above and shown e.g. in FIGS. 1 to 5. The design structures processed and/or generated by design flow 700 may be encoded on machine-readable transmission or storage media to include data and/or instructions that when executed or otherwise processed on a data processing system generate a logically, structurally, mechanically, or otherwise functionally equivalent representation of hardware components, circuits, devices, or systems. Machines include, but are not limited to, any machine used in an IC design process, such as designing, manufacturing, or simulating a circuit, component, device, or system. For example, machines may include: lithography machines, machines and/or equipment for generating masks (e.g. e-beam writers), computers or equipment for simulating design structures, any apparatus used in the manufacturing or test process, or any machines for programming functionally equivalent representations of the design structures into any medium (e.g. a machine for programming a programmable gate array).

Design flow 700 may vary depending on the type of representation being designed. For example, a design flow 700 for building an application specific IC (ASIC) may differ from a design flow 700 for designing a standard component or from a design flow 700 for instantiating the design into a programmable array, for example a programmable gate array (PGA) or a field programmable gate array (FPGA) offered by Altera® Inc. or Xilinx® Inc.

FIG. 7 illustrates multiple such design structures including an input design structure 720 that is, for example, processed by a design process 710. Design structure 720 may be a logical simulation design structure generated and processed by design process 710 to produce a logically equivalent functional representation of a hardware device. Design structure 720 may also or alternatively comprise data and/or program instructions that when processed by design process 710, generate a functional representation of the physical structure of a hardware device. Whether representing functional and/or structural design features, design structure 720 may be generated using electronic computer-aided design (ECAD) such as implemented by a core developer/designer. When encoded on a machine-readable data transmission, gate array, or storage medium, design structure 720 may be accessed and processed by one or more hardware and/or software modules within design process 710 to simulate or otherwise functionally represent an electronic component, circuit, electronic or logic module, apparatus, device, or system such as those shown in FIGS. 1 to 5. As such, design structure 720 may comprise files or other data structures including human and/or machine-readable source code, compiled structures, and computer-executable code structures that when processed by a design or simulation data processing system, functionally simulate or otherwise represent circuits or other levels of hardware logic design. Such data structures may include hardware-description language (HDL) design entities or other data structures conforming to and/or compatible with lower-level HDL design languages such as Verilog and VHDL, and/or higher level design languages such as C or C++.

Design process 710, for example, employs and incorporates hardware and/or software modules for synthesizing, translating, or otherwise processing a design/simulation functional equivalent of the components, circuits, devices, or logic structures shown in FIGS. 1-5 to generate a Netlist 780 which may contain design structures such as design structure 720. Netlist 780 may comprise, for example, compiled or otherwise processed data structures representing a list of wires, discrete components, logic gates, control circuits, I/O devices, models, etc. that describes the connections to other elements and circuits in an integrated circuit design. Netlist 780 may be synthesized using an iterative process in which netlist 780 is resynthesized one or more times depending on design specifications and parameters for the device. As with other design structure types described herein, netlist 780 may be recorded on a machine-readable data storage medium or programmed into a programmable gate array. The medium may be a non-volatile storage medium such as a magnetic or optical disk drive, a programmable gate array, a compact flash, or other flash memory. Additionally, or in the alternative, the medium may be a system or cache memory, buffer space, or electrically or optically conductive devices and materials on which data packets may be transmitted and intermediately stored via the Internet, or other networking suitable means.

Design process 710 may include hardware and software modules for processing a variety of input data structure types including Netlist 780. Such data structure types may reside, for example, within library elements 730 and include a set of commonly used elements, circuits, and devices, including models, layouts, and symbolic representations, for a given manufacturing technology (e.g., different technology nodes, 32 nm, 45 nm, 90 nm, etc.). The data structure types may further include design specifications 740, characterization data 750, verification data 760, design rules 770, and test data files 785 which may include input test patterns, output test results, and other testing information. Design process 710 may further include, for example, standard mechanical design processes such as stress analysis, thermal analysis, mechanical event simulation, process simulation for operations such as casting, molding, and die press forming, etc. One of ordinary skill in the art of mechanical design can appreciate the extent of possible mechanical design tools and applications used in design process 710 without deviating from the scope and spirit of the invention. Design process 710 may also include modules for performing standard circuit design processes such as timing analysis, verification, design rule checking, place and route operations, etc.

Design process 710 employs and incorporates logic and physical design tools such as HDL compilers and simulation model build tools to process design structure 720 together with some or all of the depicted supporting data structures along with any additional mechanical design or data (if applicable), to generate a second design structure 770. Design structure 790 resides on a storage medium or programmable gate array in a data format used for the exchange of data of mechanical devices and structures (e.g. information stored in a IGES, DXF, Parasolid XT, JT, DRG, or any other suitable format for storing or rendering such mechanical design structures). Similar to design structure 720, design structure 790, for example, comprises one or more files, data structures, or other computer-encoded data or instructions that reside on transmission or data storage media and that when processed by an ECAD system generate a logically or otherwise functionally equivalent form of one or more of the embodiments of the invention shown in FIGS. 1 to 5. In one embodiment, design structure 790 may comprise a compiled, executable HDL simulation model that functionally simulates the devices shown in FIGS. 1-5.

Design structure 790 may also employ a data format used for the exchange of layout data of integrated circuits and/or symbolic data format (e.g. information stored in a GDSII (GDS2), GL1, OASIS, map files, or any other suitable format for storing such design data structures). Design structure 790 may comprise information such as, for example, symbolic data, map files, test data files, design content files, manufacturing data, layout parameters, wires, levels of metal, vias, shapes, data for routing through the manufacturing line, and any other data required by a manufacturer or other designer/developer to produce a device or structure as described above and shown in FIGS. 1-5. Design structure 790 may then proceed to a stage 795 where, for example, design structure 790: proceeds to tape-out, is released to manufacturing, is released to a mask house, is sent to another design house, is sent back to the customer, etc.

Figure 8:
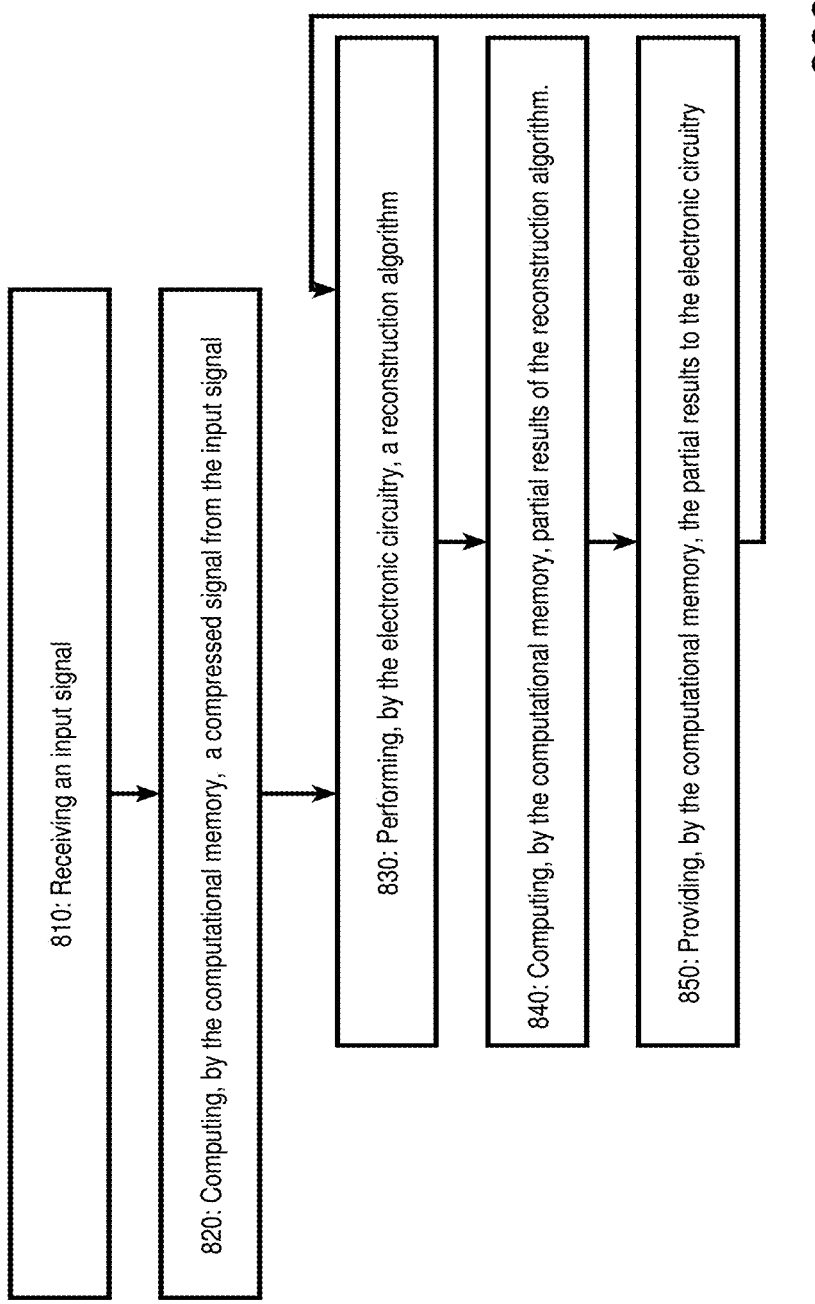
FIG. 8 shows a flowchart of method steps of a method for signal compression and reconstruction.

FIG. 8 shows a flowchart of method steps of a method 800 for signal compression and reconstruction. The sensor device comprises a computational memory and electronic circuitry and may be embodied as described above with reference to FIGS. 1 to 5.

At a step 810, the sensor device receives an input signal, e.g. a measurement signal measured by the sensor device.

At a step 820, the computational memory computes a compressed signal from the input signal.

At a step 830, the electronic circuitry performs a reconstruction algorithm to compute a reconstructed signal from the compressed signal.

At a step 840, the computational memory computes partial results of the reconstruction algorithm.

At a step 850, the computational memory provides the partial results to the electronic circuitry which may use them for the further execution of the reconstruction algorithm.

The steps 830, 840 and 850 may be repeated in an iterative manner.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In general, modifications described for one embodiment may be applied to another embodiment as appropriate.

What is claimed is:

1. A sensor device comprising
a computational memory; and
electronic circuitry;
the sensor device being configured to
receive an input signal;
compress the input signal into a compressed signal; and
compute a reconstructed signal from the compressed signal;
wherein the electronic circuitry is configured to perform a reconstruction algorithm to compute the reconstructed signal; and
the computational memory is configured to compute the compressed signal and partial results of the reconstruction algorithm, wherein
the computational memory comprises at least one memristive array comprising a plurality of resistive memory elements, the resistive memory elements being arranged in a crossbar topology.

2. A sensor device according to claim 1, wherein
the electronic circuitry is configured to
apply programming signals to the resistive memory elements to program conductance values as a measurement matrix; and
the computational memory is configured to
compress the input signal by performing a matrix-vector multiplication of the input signal with the measurement matrix; and
compute the partial results of the reconstruction algorithm by performing matrix-vector multiplications with the measurement matrix.

3. A sensor device according to claim 2, wherein the electronic circuitry is configured to program the conductance values of the resistive memory elements by an iterative program and verify procedure.

4. A sensor device according to claim 1, wherein
the memristive array comprises
a plurality of row lines;
a plurality of columns lines; and
a plurality of junctions arranged between the plurality of row lines and the plurality of column lines, wherein each junction comprises a programmable resistive memory element.

5. A sensor device according to claim 4, wherein
the electronic circuitry comprises a readout circuit configured to
apply read voltages to the row lines and/or column lines of the memristive array;
read out current values of the row lines and/or column lines of the memristive array; wherein
the read voltages represent vector values of a vector of a matrix-vector multiplication; and
the current values represent result values of vector elements of a product vector of the matrix-vector multiplications.

6. A sensor device according to claim 4, wherein the plurality of junctions comprise a serial arrangement of a resistive memory element and a transistor.

7. A sensor device according to claim 1, wherein the computational memory comprises a first memristive array for programming a measurement matrix and a second memristive array for programming a transpose of the measurement matrix.

8. A sensor device according to claim 1, wherein the reconstruction algorithm is an approximate message passing algorithm.

9. A sensor device according to claim 1, wherein the reconstruction algorithm comprises an integrated de-noising functionality.

10. A sensor device according to claim 1, wherein the device is configured to perform a block-based compression and reconstruction.

11. A sensor device as claimed in claim 1, wherein the resistive memory elements are one of Phase change memory (PCM) elements, Conductive bridge resistive memory elements, Metal-oxide resistive random access memory (RRAM) elements, Magneto-resistive random access memory (MRAM) elements, Ferroelectric random access memory (FeRAM) elements, optical memory elements, and a system device, the system device comprising transistors, resistors, capacitors, and/or inductors configured to jointly emulate a behavior of a resistive memory element.

12. A sensor device as claimed in claim 11, wherein the resistive memory elements are phase change memory elements and wherein the device is configured to:
apply a Reset-pulse to the phase change memory elements in order to bring the phase change memory elements in the amorphous state;
apply as programming signals current pulses to the phase change memory elements that heat the phase change memory elements above the crystallization temperature, thereby lowering the conductance of the phase change memory elements to a desired conductance value.

13. A method for signal compression and reconstruction, the method comprising:
receiving, by a sensor device, an input signal, the sensor device comprising at least a computational memory and electronic circuitry, wherein the computational memory comprises at least one memristive array comprising at least a plurality of resistive memory elements, the resistive memory elements being arranged in a crossbar topology;
computing, by the computational memory, a compressed signal from the input signal;
performing, by the electronic circuitry, a reconstruction algorithm to compute a reconstructed signal from the compressed signal;

computing, by the computational memory, partial results of the reconstruction algorithm; and providing, by the computational memory, the partial results to the electronic circuitry.

14. A method according to claim 13, further comprising applying programming signals to the resistive memory elements of the computational memory to program conductance values as a measurement matrix;

compressing the input signal by performing a matrix-vector multiplication of the input signal with the measurement matrix; and computing the partial results of the reconstruction algorithm by performing matrix-vector multiplications with the measurement matrix.

15. A method according to claim 13, further comprising:

applying read voltages to row lines and/or column lines of the memristive array of the computational memory;

reading out current values of the row lines and/or column lines of the memristive array; wherein the read voltages represent vector values of a vector of a matrix-vector multiplication; and the current values represent result values of vector elements of a product vector of the matrix-vector multiplication.

16. A method according to claim 13, wherein the reconstruction algorithm is an approximate message passing algorithm.

17. A design structure tangibly embodied in a machine readable medium for designing, manufacturing, or testing an integrated circuit, the design structure comprising:

a sensor device comprising a computational memory and electronic circuitry;

the sensor device being configured to
receive an input signal;
compress the input signal into a compressed signal; and
compute a reconstructed signal from the compressed signal;

wherein the electronic circuitry is configured to perform a reconstruction algorithm to compute the reconstructed signal; and the computational memory is configured to compute the compressed signal and partial results of the reconstruction algorithm, wherein the computational memory comprises at least one memristive array comprising a plurality of resistive memory elements, the resistive memory elements being arranged in a crossbar topology.

18. A design structure according to claim 17, wherein the memristive array comprises:

a plurality of row lines;

a plurality of columns lines; and a plurality of junctions arranged between the plurality of row lines and the plurality of column lines, wherein each junction comprises a programmable resistive memory element.

* * * * *